United States Patent
LaBorde-Boutet et al.

(10) Patent No.: US 10,408,743 B2
(45) Date of Patent: Sep. 10, 2019

(54) IN SITU ANALYSIS OF PETROLEUM STABILITY

(71) Applicant: THE GOVERNORS OF THE UNIVERSITY OF ALBERTA, Edmonton (CA)

(72) Inventors: Cedric LaBorde-Boutet, Edmonton (CA); William McCaffrey, Edmonton (CA)

(*) Notice: Subject to any disclaimer, the term of this patent is extended or adjusted under 35 U.S.C. 154(b) by 0 days.

(21) Appl. No.: 15/579,567

(22) PCT Filed: Jun. 6, 2016

(86) PCT No.: PCT/CA2016/050643
§ 371 (c)(1),
(2) Date: Dec. 4, 2017

(87) PCT Pub. No.: WO2016/191889
PCT Pub. Date: Dec. 8, 2016

(65) Prior Publication Data
US 2018/0172579 A1    Jun. 21, 2018

Related U.S. Application Data

(60) Provisional application No. 62/171,809, filed on Jun. 5, 2015.

(51) Int. Cl.
*G01N 21/27* (2006.01)
*G01N 21/25* (2006.01)
(Continued)

(52) U.S. Cl.
CPC .............. *G01N 21/27* (2013.01); *G01N 21/25* (2013.01); *G01N 21/251* (2013.01);
(Continued)

(58) Field of Classification Search
CPC ...... G01N 21/27; G01N 21/251; G01N 21/21; G01N 33/2805; G06T 7/90
See application file for complete search history.

(56) References Cited

U.S. PATENT DOCUMENTS 6,690,453 B2   2/2004   Mougin
8,398,849 B2   3/2013   Cross et al.
(Continued)

OTHER PUBLICATIONS

Bagheri, S. R.; Gray, M. R.; McCaffrey, W. C. Influence of Depressurization and Cooling on the Formation and Development of Mesophase. Energy Fuels, 2011, 25, 5541-5548.*
(Continued)

*Primary Examiner* — Maurice C Smith
(74) *Attorney, Agent, or Firm* — Bennett Jones LLP

(57) ABSTRACT

A method of evaluating formation of fouling material in a petroleum feed involves illuminating a sample with cross-polarized light while subjecting the sample to temperature and pressure conditions relevant to an industrial process to induce chemical and/or physical changes; collecting images of the treated sample; and analyzing the images to evaluate fouling formation based on heterogeneity of the images in terms of brightness and/or color, where an increase in heterogeneity is indicative of initiation of fouling formation. The method is conducted using a cross-polarized microscopy system including a hot stage reactor assembly capable of withstanding operation within a temperature between about 20° C. to 450° C. or higher, and a pressure between about 0.1 MPa to 16 MPa or higher.

14 Claims, 9 Drawing Sheets

(51) Int. Cl.
*G01N 21/85* (2006.01)
*G01N 33/28* (2006.01)

(52) U.S. Cl.
CPC ........... *G01N 21/255* (2013.01); *G01N 21/85* (2013.01); *G01N 33/2805* (2013.01)

(56) References Cited

U.S. PATENT DOCUMENTS

2006/0014296 A1 1/2006 Brons et al.
2009/0326383 A1* 12/2009 Barnes ................. A61B 5/0059
600/476

OTHER PUBLICATIONS

Bagheri et al., Energy Fuels, 2012, 4978.
Bagheri et al., Energy Fuels, 2012, 3167.
Gray, M. R. Upgrading Petroleum Residues and Heavy Oils; Marcel Dekker Inc.: New York, USA, 1994.
Wiehe, I. A. Process Chemistry of Petroleum Macromolecules; CRC Press: Boca Raton, USA, 2008.
Wiehe, I. A.; Kennedy, R. J. Application of the Oil Compatibility Model to Refinery Streams. Energy Fuels, 2000, 14, 60-63.
Wiehe, I. A. A Phase-Separation Kinetic Model for Coke Formation. Ind. Eng. Chem. Res., 1993, 32, 2447-2454.
Bagheri, S. R.; Gray, M. R.; Shaw, J.; McCaffrey, W. C. In Situ Observation of Mesophase Formation and Coalescence in Catalytic Hydroconversion of Vacuum Residue Using a Stirred Hot-Stage Reactor. Energy Fuels, 2012, 26, 3167-3178.
Bagheri, S. R.; Gray, M. R.; McCaffrey, W. C. Depolarized Light Scattering for Study of Heavy Oil and Mesophase Formation Mechanisms. Energy Fuels, 2012, 26, 5408-5420.
Brooks, J. D.; Taylor, G. H. Formation of Graphitizing Carbons from the Liquid Phase. Nature, 1965, 32, 697-699.
Chwastiak, S.; Lewis, R. T.; Ruggiero, J. D. Quantitative Determination of Mesophase Content in Pitch. Carbon, 1981, 19, 357-363.
R.T. Lewis. Hot-Stage Microscopy of Mesophase Pitches. Ext. Abstr. 12th Bienn. Am. Conf. Carbon, Am. Carbon Soc. 1975, 215-216.
Perrotta, A. J.; McCullough, J. P.; Beuther, H. Pressure-Temperature Microscopy of Petroleum-Derived Hydrocarbons. Prepr. Pap. Am. Chem. Soc., Div. Pet. Chem., 1983, 28, 633-639.
Lafdi, K.; Bonnamy, S.; Oberlin, A. Mechanism of Anisotropy Occurrence in a Pitch Precursor of Carbon-Fibers : 3. Hot Stage Microscopy of Pitch-B and Pitch-C. Carbon, 1991, 29, 857-864.
Rahimi, P.; Gentzis, T.; Dawson, W. H.; Fairbridge, C.; Khulbe, C.; Chung, K.; Nowlan, V.; DelBianco, A. Investigation of Coking Propensity of Narrow Cut Fractions from Athabasca Bitumen Using Hot-Stage Microscopy. Energy Fuels, 1998, 12, 1020-1030.

* cited by examiner

IN SITU ANALYSIS OF PETROLEUM STABILITY

FIELD OF THE INVENTION

The present invention relates to a method for analyzing stability of petroleum feeds under refining or upgrading reaction conditions.

BACKGROUND OF THE INVENTION

In the petroleum industry, refining and upgrading oils into lighter products is carried out in several reactive and separation stages. The heavier fractions of different feeds can exhibit a wide diversity of phase behaviors in various refining or upgrading processes such as visbreaking or hydroconversion. In such processes, phase separation which can lead to uncontrolled formation of coke or sediments is highly undesirable, as the reactor, along with upstream and downstream units would become fouled. Fouling in oil processing units and lines causes a loss of throughput as well as a loss of heat transfer efficiency, and can lead to plugging with attendant shutdown, cleanup, and maintenance costs. Therefore, it is desired to optimize operating conditions in order to obtain the maximum conversion without yielding a product where phase separation would occur. Finding optimum conditions when having to process various feeds and blends with ill-defined properties can be problematic.

The formation of fouling material from petroleum thermal cracking and hydrogen addition processes is largely due to the solubility limit of reacted asphaltenes. Thermal cracking of petroleum macromolecules induces the formation of large hydrogen-deficient poly-aromatic species which may no longer be solvated by products having lower molar mass and aromaticity. Additionally, the differential in molecular solubility parameters of the constituents in the liquid cracking phase can be strongly affected by changes in process pressure, which may cause precipitation in fractionators following hydroconversion units.

The fouling behavior of reacting residues has been observed in situ. More specifically, the onset time of coke formation (also referred to as "induction period") was characterized by the detection of anisotropic carbonaceous material with liquid crystalline properties, which has been designated as "mesophase". Since anisotropic mesophase exhibits optical activity, cross-polarized microscopy is an appropriate method for examining the phase behavior of petroleum at elevated temperatures.

In situ observations of thermal cracking reactions in Athabasca Vacuum Residue has revealed a gradual darkening of the oil sample with reaction time until the onset of mesophase. Being anisotropic, mesophase material formed brighter domains whose growth affected the darkening rate of the whole image of the reacting residue. Thus, it was concluded that identifying a change of slope in the Mean Brightness Intensity vs. Reaction Time trend could provide a fair estimate of the fouling onset time in a thermal cracking process. However, this analysis has proven not to be applicable to all cases of phase instability, as it was only focused on the detection of anisotropic mesophase coke.

While changes in overall image brightness are strongly correlated to the conversion of the oil into products, these changes do not provide much insight regarding the stability of reacting oils at elevated temperatures. Accordingly, there is a need in the art for an improved method for analysis of petroleum stability under the operating conditions of refinery or upgrading units.

SUMMARY OF THE INVENTION

Aspects of the present invention are based on the characterization of the chemical and physical events prior to the formation of mesophase, by evaluating changes in spectral properties of reflected light over time under refining or upgrading process conditions.

In one aspect, the invention comprises a method of determining stability of a petroleum feed, comprising the steps of obtaining spectral properties of reflected light over time under reaction conditions, analyzing the data and detecting an increase in a measure of heterogeneity. In one embodiment, the spectral data comprises a digital image comprising pixelated RGB or HSI information, and the increase in heterogeneity is manifest as a red-to-blue color shift. Without restriction to a theory, it is believed this increase in heterogeneity and/or color shift corresponds to the formation of a fouling layer of isotropic coke, toluene insoluble material, or carbon disulfide ($CS_2$) insoluble material. The increase in heterogeneity or beginning of the color shift precedes the formation of mesophase. Methods of the present invention may provide an improved solution for testing the fouling propensity of a feed or for developing online sensors operating in industrial units.

Therefore, in one aspect, the invention comprises a method of determining the propensity of a petroleum feed to form fouling material, comprising the steps of:
a) subjecting a sample of the petroleum feed to process conditions to induce one or more chemical and/or physical changes, while illuminating the sample with cross-polarized light;
b) collecting light reflected by the sample over a period of time; and
c) analyzing spectral properties of the collected light and determining:
  1. a measure of heterogeneity of the sample, where an increase in heterogeneity is indicative of initiation of fouling formation; and/or
  2. a measure of color of the sample, where a shift from red to blue is indicative of initiation of fouling material formation.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
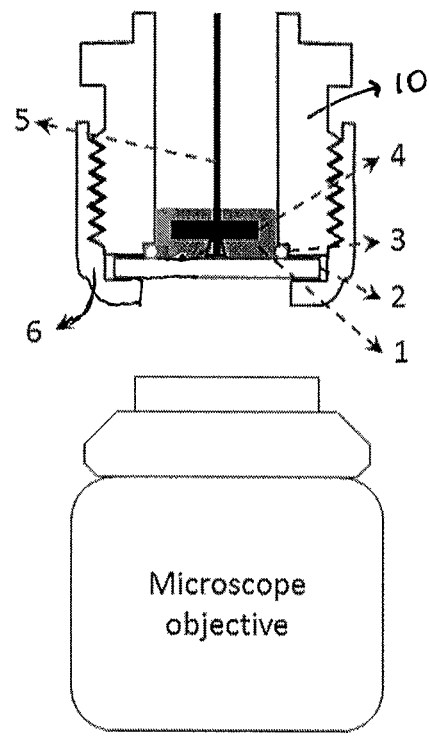
FIG. 1 is a schematic diagram of a high-pressure optical hot-stage reactor assembly which may be used to perform an in situ method of the present invention.

The present invention relates to an improved method for analyzing petroleum stability using a reactor under operating conditions similar those in a refining or upgrading process. While processing petroleums, it is desirable to avoid the formation of fouling material or foulant. Determining the point of instability under in-situ conditions for a particular petroleum feed may be beneficial to avoiding the onset of fouling material formation in a refining or upgrading process. Embodiments of the present invention may provide methods of determining the point of instability of a petroleum feed by analyzing images obtained using in situ cross-polarized imagery. Such analysis reveals two strong correlations: sample conversion correspond to brightness intensity; and solubility properties are linked to heterogeneity and/or color changes.

As used herein, a "petroleum feed" includes any mix of hydrocarbons which may undergo refining or upgrading process to produce useful products. For example, heavy oil may be upgraded to synthetic light crude oil. In another example, light crude oil may be refined into useful products such as naptha, gasoline, kerosene, diesel oil, and gas oils. Gas oils may be further processed and converted to lighter products, such as by hydrocracking. Residual hydrocarbons, the heaviest components, may be coked to produce lighter products and petroleum coke.

As used herein, the term "reaction" may include physical changes as well as chemical changes or reactions. For example, a reaction may include phase changes or a solubility changes which occur in a feed, or a component of a feed, during a process. "Stability" refers to the ability of a petroleum feed to resist physical and/or chemical change with changing process conditions or over time. A point of instability may be the combination of conditions where an undesirable physical or chemical change begins to occur in a petroleum feed. A more stable feed will have a lower propensity to form fouling material.

As used herein, the term "mesophase" refers to a state of matter intermediate between liquid and solid. In the context of upgrading of heavy feeds, "mesophase" is an aromatic dense phase that is formed upon the heat treatment of petroleum pitch in the temperature range of about 350-500° C., which is optically anisotropic.

As used herein, the term "cross-polarized microscopy" refers to a polarizing microscopy technique capable of distinguishing between isotropic and anisotropic materials like liquid crystals.

The coloration of a crude oil essentially results from the overlapping spectra of the wide diversity of constituents within the oil. The absorption of visible light by hydrocarbon molecules follows electronic excitation mechanisms with low transition energies, where more conjugated species absorb more strongly at longer wavelengths. The nature and location of heteroatoms can also be a factor in the coloration of a feed, Therefore, any reactions that increase conjugation, such as increasing aromaticity, should modify the reflected color of oil samples.

Fouling material includes anisotropic mesophase coke which forms in thermal treatment processes of heavy oil, such as visbreaking, coking or hydroconversion. However, formation of mesophase coke is generally preceded by the formation of isotropic coke and/or $CS_2$ insoluble materials. Isotropic coke comprises toluene-insoluble material which is present or which forms in a petroleum feed, Therefore, methods of the present invention include methods of detecting the formation of coke, isotropic coke, toluene-insoluble material and/or $CS_2$ insoluble materials.

Reactor

In one embodiment, the method may be implemented with a reactor with a cross-polarized microscopy system which allows a reaction to be followed in real-time. The system may comprise a high-pressure cell for use on a stage of an inverted reflective optical microscope (FIG. 1). A light collecting device comprising a camera, spectrometer or hyperspectral analyzer is connected to the microscope to collect spectral data representing the progress of the reaction. Spectral data may include a spectral curve across a wide spectrum of wavelengths for each location under observation, and may include conventional pixelated digital photographic data. When characterized photographically, the analysis of the images may be performed with a computer to determine optical properties of the sample in each image.

In one embodiment, the reactor includes a reactor body (10), a window (2); a sealing ring (3) disposed between the window and the body; a magnet (4); a thermocouple (5); and a locking ferrule or nut (6) to secure the window (2) against the body (10). The sample (1) is placed in the reactor and is typically a liquid at the temperature and pressure range of interest. A microscope is inverted below the reactor assembly as shown in FIG. 1. In some embodiments, it is important that the sample (1) wet the window (2).

The components of the reactor are chosen for their ability to withstand reaction conditions which may include extreme pressure and temperature. For example, the body may comprise stainless steel tubing, or another high temperature alloy, while the window may comprise sapphire. Preferably Swagelok™ fittings are used to construct the reactor.

The seal is compressed between the body and the window by tightening the bottom nut (6) which is threaded onto the body (10). In one embodiment, the seal comprises an O-ring (3) which may comprise a silver-plated stainless steel O-ring, or a ring having a C-shaped cross-section (a C-ring) seal. In one embodiment, a C-ring seal is formed of a suitable metal such as stainless steel. The groove defined by the body is adapted to receive and accommodate the dimensions of the C-ring seal. The C-ring seal may withstand operational temperature and pressure ranges of up to about 450° C., and to about 16 MPa. The C-ring seal offers high spring-back capabilities which maintain the seal at high temperature, where high pressure conditions actually facilitate the sealing process by urging the seal against the body. As well, thermal expansion does not affect a C-ring seal as much as an O-ring.

The reactor may be heated by any suitable means and is thermally insulated by ceramic covers. Heating tape (not shown) may be used to heat the reactor, however heating tape may have limited heating rate, and may be prone to short-circuiting due to rapid wear of the cables within the heating tape. In a preferred embodiment, the reactor is heated with a coil heater (not shown), using a heat transfer element between the coil heater and the reactor, such as a metal block. The coil heater is encased by ceramic wool for insulation to withstand temperatures up to about 450° C. without having to operate at full power output. A temperature regulator may be used for controlling the power supply to the coil heater, based on the temperature in the reactor sensed by the thermocouple, which is in direct contact with the inside surface of the window.

In one embodiment, the window may comprise any material transparent to the spectrum being collected, such as optically transparent silica glass or ceramics such as YAG (yttrium aluminum garnet). In order to collect images of isotropic materials, a birefringent material such as sapphire is necessary. Any crystal orientation of sapphire is suitable, however the liquid sample must be wetted against the window.

The reactor is connected with an inlet to a source of gas (eg. hydrogen or nitrogen) pressure to pressurize the head space above the sample (1), and a vent line to purge the reactor.

The magnet (4) is preferably an alnico magnet, which allows magnetic stirring by coupling to a magnet outside the reactor which is mechanically rotated. However, the magnetic coupling between the two magnets is sometimes inefficient as the outside magnet must be located away from the reactor in order to allow enough space for the heater and insulating elements, and the heater surrounding the reactor acts as a magnetic shield, creating a hindrance to the magnetic coupling. Therefore, in a preferred embodiment, a magnetic stirring assembly includes a shaft rotating around the thermocouple, the shaft having impeller blades at the bottom and a magnet at the top. The magnet is located above the heater so that the outside magnets can be rotated closer to the inside magnet. The magnetic stirring assembly is positioned to allow clearance between the top surface of the sapphire window and the bottom of the impeller blades to avoid obstructing visualization of fouling material. In one embodiment, the clearance ranges from about 2 mm to about 3 mm.

In one embodiment, the reactor comprises an adsorbent assembly positioned between the reactor and a vent line for collecting light volatile components resulting from reactions of petroleum and emanating from the reaction chamber. This may permit in situ analysis of the effect of removal of such light volatile components during the process. In one embodiment, the adsorbent assembly comprises one or more gasket face seal fittings, suitably formed of stainless steel or other metal to provide leak-tight service from vacuum to positive pressure. In one embodiment, the adsorbent comprises an activated charcoal or zeolite which adsorbs light volatile petroleums, Each of the meshed gaskets provides a fine grid which keeps the adsorbent within the assembly regardless of the gas flowing through.

Typically, a test requires constant pressure; however, pressure fluctuations may occur in a process unit due to temperature changes (i.e., higher temperature inducing a pressure increase) or reactive processes (i.e., production or consumption of gases). Therefore, in a preferred embodiment, the reactor comprises a pressure regulator for maintaining a constant pressure in the system, or for varying the pressure to simulate conditions in a high pressure separator. In one embodiment, the back-pressure regulator is set to vent a minimal flow of gas under setpoint pressure conditions, but increases the vented flowrate at higher pressure. A constant head of high pressure is maintained on the reactor. Over-pressurizing (as a result of heating) may be remedied by venting out the excess pressure, while under-pressurizing (as a result of hydrogen gas consumption by the reaction) may be minimized as the back-pressure regulator stops venting if the pressure falls below predetermined setpoint conditions.

In one embodiment, the reactor of the present invention comprises one or more safety features selected from a minimized reactor headspace, a rupture disc line, an acoustic enclosure, or a flow limiter. Since the reactor may be operable at high gas pressure conditions (about 16 MPa), these safety features minimize the risk of damage and injury in the event of a catastrophic system failure such as, for example, explosion caused by the sudden decompression of highly pressurized gas.

It is preferred to minimize the total internal volume of the reactor assembly as only a small volume of liquid phase, for example about 0.6 ml, is on the window is under observation during a test. The remainder of the reactor volume, above that occupied by the liquid phase, is gas headspace. Reduction of the headspace may reduce the energy released by sudden decompression of highly pressurized gas (about 16 MPa) in the event of system failure. If a flammable gas might be used, the fire hazard would also be considerably reduced with a small reactor headspace. Therefore, in one embodiment, the minimized headspace comprises an estimated total volume of less than about 10 ml, and preferably less than about 7 ml.

In one embodiment, the reactor may comprise a rupture disc line to prevent a catastrophic system failure in the event of an uncontrolled pressure surge. In one embodiment, the rupture disc comprises an angular rupture disc designed to rupture at about 3000 psi at room temperature. At about 450° C., the point of rupture of the disc drops to about 2700 psi. This pressure threshold may be set slightly above the maximum operating pressure of the reactor, but still below the pressure level of catastrophic failure.

In one embodiment, the reactor is enclosed in an acoustic enclosure, to minimize the consequences of a catastrophic failure. In one embodiment, the acoustic enclosure comprises a box formed of aluminum layered with acoustic foam material. The enclosure may be mounted on the microscope and encase the reactor.

In one embodiment, the reactor may comprise a flow limiter positioned between the gas cylinder and the inlet line of the reactor. The flow limiter may comprise capillary tubing having a reduced inner diameter, such as in the range of about 0.005 inches. The flow limiter constrains the gas flow-rate to minimal levels while operating at high pressures in order to limit the release of flammable gas in the event of a catastrophic system failure.

A light-collecting device is positioned to allow for the acquisition of spectral data as the sample is subjected to reaction conditions. The device may be a hyperspectral sensor, a spectrometer or a digital image capture device such as a high resolution digital camera. CMOS (complementary metal-oxide semiconductor) or CCD (charge coupled device) cameras are well known in the art. An internal illumination source is directly connected to the optical path of the microscope. The image capture device is preferably a CCD camera due to its ability to capture high quality, low noise images. The captured images are transmitted to a computer for analysis. In an alternative embodiment, the image capture device is an imaging spectrophotometer which acquires space resolved spectral data of the sample and transmits the corresponding data to a computer. A spectrometer or hyperspectral sensor may provide spectral data as a datacube where x and y represent the two spatial dimensions of the window, while the third dimension ($\lambda$) represents the spectral dimension. The light may be collected as a series of still images, as a video stream, or a continuous stream of data.

Using a reactor system as described above, a series of spectral data obtained over time, which may be in the form of digital image micrographs, for example .jpg or .png files, may be obtained. Preferably, artifacts which could affect the quality of the images should be eliminated prior to imaging. Since heat exposure of the microscope optics has a significant impact on image brightness, this parameter has to be controlled through various ways including, for example, rotating the microscope objective nosepiece to position the objective under the reactor whenever an image is desired, and rotating the nosepiece to position the objective away from the reactor when an image is not required. Various elements of the microscope (for example, the aperture diaphragm slider, iris stop slider, analyzer slider) can be set to provide steady and consistent illumination. Elements in the optical paths should be inspected and cleaned regularly to minimize artifacts.

The data recorder or image capture device is operatively connected to a host computer remote from the microscope. As used herein, the term "operatively connected" means, in the case of hardware, an electrical connection, for example, wire or cable, for conveying electrical signals, or in the case of firmware or software, a communication link between the processor (which executes the firmware—i.e., operating under stored program control—or software) and another device for transmitting/receiving messages or commands.

The computer may comprise any desktop computer, laptop computer, a handheld or tablet computer, or a personal digital assistant, and is programmed with appropriate software, firmware, a microcontroller, a microprocessor or a plurality of microprocessors, a digital signal processor or other hardware or combination of hardware and software known to those skilled in the art. The application software may comprise a program running on the computer, a web service, a web plug-in, or any software running on a specialized device, to enable the images to be processed and analyzed. The computer provides a user interface for implementing a method as described below.

Methods

In one aspect, the invention comprises a method of determining the propensity of a petroleum feed to form fouling material, comprising the steps of:
 a) subjecting a sample of the petroleum feed to reaction conditions to induce one or more chemical and/or physical changes, while illuminating the sample with cross-polarized light;
 b) collecting light reflected by the sample over a period of time; and
 c) analyzing spectral properties of the collected light and determining:
  1. a measure of heterogeneity of the sample, where an increase in heterogeneity is indicative of initiation of fouling formation; and/or
  2. a measure of color of the sample, where a shift from red to blue is indicative of initiation of fouling material formation.

Digital image (micrograph) information may be summarized by its average brightness, i.e., the average of the R, G, B values of each pixel, averaged over all the pixels of the micrographs. However, average brightness only provides limited information, and some samples exhibit no darkening with reaction time until the formation of a layer of dark fouling material, while other samples exhibited a fouling behavior where the formation of the fouling impacted color rather than brightness.

In one embodiment, heterogeneity and/or color information may be used to detect the onset of isotropic coke formation since color absorption depends on molecular conjugation, therefore, one method of the present invention provides color mapping of images for analysis. In one embodiment, the method comprises measurement of the heterogeneity of the image in terms of brightness and/or color, and plots these heterogeneity descriptors versus reaction time or temperature.

Figure 2:
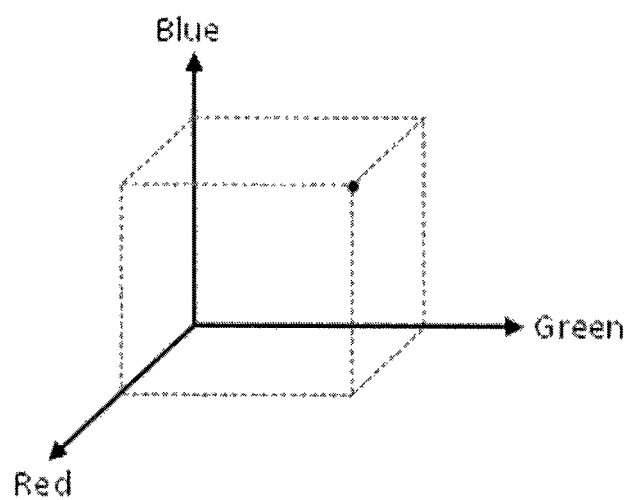
FIG. 2 shows a representation of Red, Green, Blue (RGB) color space.
Figure 3:
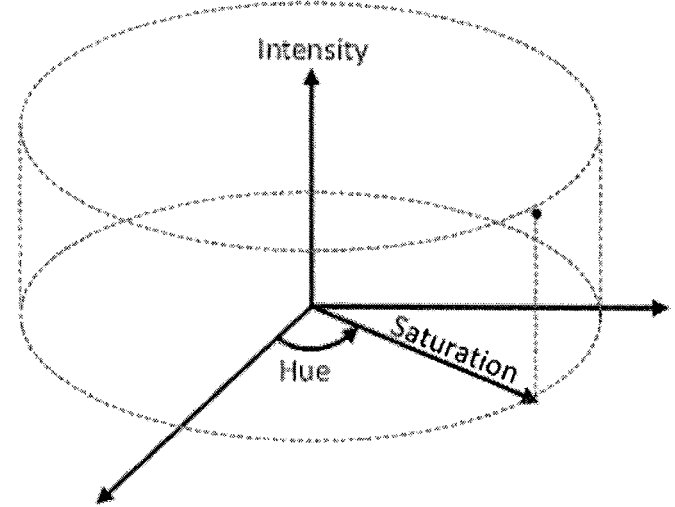
FIG. 3 shows a representation of Hue, Saturation, Intensity (HSI) color space. Hue of a pixel corresponds to the angular coordinate, defined in the $]-\pi, \pi]$ interval, Saturation of a pixel corresponds to the radial coordinate, defined in the [0,1] interval, and Intensity of a pixel corresponds to the vertical coordinate, defined in the [0,255] interval.

The evolution of the sample images may be characterized by analyzing the color and the brightness of the corresponding micrographs. Color information may be initially obtained in the individual Red, Green, Blue (RGB) values, which is the color-space defining digital images (each of the Red, Green, and Blue values ranges between 0 and 255, defining $256^3$ possible colors). In RGB color-space, shown schematically in FIG. 2, a color point is defined by Cartesian coordinates. However, it can be difficult to describe perceptually relevant information about color changes when using RGB values, especially if a change in brightness takes place simultaneously. Therefore, in one embodiment, image characterization may be translated into a color-space defined by Hue, Saturation, and Intensity (HSI), which provides a more intuitive description of color as perceived by the human eye. Hue indicates a type of "pure" color, as would be given by a line on the spectrum of visible light. Saturation is the colorfulness of a stimulus relative to its own brightness; in other words low Saturation levels correspond to greyish colors while high Saturation levels correspond to vibrant colors. The Intensity simply describes the brightness of an image. In HSI color-space, shown in FIG. 2B, a color point is defined by cylindrical coordinates, where Hue is the angular coordinate, Saturation is the radial coordinate, and Intensity is the vertical coordinate. A disc covered by Hue and Saturation values is traditionally called a "colorwheel", shown schematically in FIG. 3. Conversion of RGB values into HSI values may be made using equations Eq. 1 to Eq. 6.

$$\alpha = \frac{1}{2}(2R - G - B) \quad \text{Eq. 1}$$

$$\beta = \frac{\sqrt{3}}{2}(G - B) \quad \text{Eq. 2}$$

$$m = \min(R, G, B) \quad \text{Eq. 3}$$

$$H = a\tan2(\beta, \alpha) \quad \text{Eq. 4}$$

$$I = \frac{1}{3}(R + G + B) \quad \text{Eq. 5}$$

$$S = \begin{cases} 0 & \text{if } m = I \\ 1 - \frac{m}{I} & \text{if } m \neq I \end{cases} \quad \text{Eq. 6}$$

The conversion of RGB to HSI involves an intermediate step that uses a pair of chromaticity coordinates, $\alpha$ and $\beta$, as well as the minimum of RGB values, m. In Eq. 4, atan2 is the arctangent function with two arguments.

Micrograph data may be expressed in terms of their mean Hue, Saturation, and/or Intensity values, i.e., their average over the ensemble of pixels which makes the entire image. Mean Hue values are circular mean values (whereas Saturation and Intensity values are arithmetic means) derived from angular data defined in the ]-π, π] interval. For example, the mean Hue between a purely green (angular data 2π/3) pixel and a purely blue (angular data—2π/3) pixel would have an angular data of it (corresponding to cyan blue) following circular statistics, whereas the arithmetic mean of these angles would be 0 (corresponding to red). Computation of mean HSI values from micrographs may be carried out by means of an algorithm coded in MATLAB environment.

One level of heterogeneity descriptors may be defined by computing the standard deviations of the H, S, and/or I values for each micrograph based on the values for all pixels, and referred to as "global H heterogeneity," "global S heterogeneity," and "global I heterogeneity". A significant inflection in one or more global heterogeneity descriptors versus time, or a process condition such as temperature or pressure, is indicative of the formation of a fouling material, resulting from phase instability, and may be visualized in a plot of standard deviation value. A significant inflection may comprise an increase in the standard deviation of 10%, 15%, or 20% or more. Alternatively, a significant inflection may comprise a minimum exhibited by a shift from a decreasing trend to an increasing trend in a heterogeneity descriptor.

Another level of heterogeneity descriptors may be defined by computing the standard deviation of the H, S, and I values for local regions of pixels, and then summing the values obtained for each local region to yield the descriptors "local H heterogeneity," "local S heterogeneity," and "local I heterogeneity". Calculating these local heterogeneity descriptors may be carried out in stages. The first stage is to define the size of the local region where statistics are to be calculated, in terms of pixels. The size of the region in terms of pixels ("D") should preferably correspond to a physical size in the reactor below about 20 μm in diameter. An iterative procedure is then performed for each pixel of the micrograph. For each pixel of the micrograph, the local standard deviations of the H, S, and I values are calculated for the local region centered on the pixel and defined by D. The following sums are calculated, with a significant increase in one or more local heterogeneity descriptors being indicative of phase instability.

Local H Heterogeneity=Σ Local standard deviations of H/Number of pixels   Eq. 7

Local S Heterogeneity=Σ Local standard deviations of S/Number of pixels   Eq. 8

Local I Heterogeneity=Σ Local standard deviations of I/Number of pixels   Eq. 9

As will be apparent to those skilled in the art, a color shift in one region of a micrograph which occurs before the color shift spreads or occurs in other regions of the micrograph, will cause or be coincidental with an increase in overall image heterogeneity. Therefore, the early observation or detection of a color shift is one specific example of an increase in heterogeneity of an image.

The determination of when a color shift occurs may be determined by plotting the evolution of color on a color wheel, and determining an apex point where the color stops moving towards red, and changes direction towards blue. Color may be determined by an average Hue and Saturation values over the entire set of pixels, or may be determined in local regions.

Spectral data may be normalized so that spectra can be compared separately from an intensity variable. Spectral data may be noisy and noise removal algorithms may be implemented by those skilled in the art. For example, noise removal may be performed using a smoothing algorithm using centred moving averages on normalized spectral values (NSV) at any given wavelength (λ, here expressed in nm):

$$NSV_{filtered}(\lambda) = \frac{1}{2 \times 5.2} \int_{\lambda-5.2}^{\lambda+5.2} NSV(\lambda) d\lambda \quad \text{Eq. 10}$$

A red-to-blue color shift may be more easily detected using spectral data rather than RGB derived values, as an increase in the range below about 490 nm in the series of normalized spectra will be accompanied by a decrease at all longer wavelengths in the visible spectrum.

EXAMPLES

Exemplary embodiments of the present invention are described to aid in the understanding of the invention, and should not be construed to limit in any way the scope of the invention as defined in the claims which follow thereafter.

In situ observations of thermal cracking reactions were performed by cross-polarized microscopy on a variety of petroleum feeds (see Table 1 below) at different temperatures. All feeds showed mean similar trends: at first, samples brightened when heated to the setpoint temperature, with negligible change in color. This brightening seemed caused by a growing difference between the refractive index of the feed and that of sapphire with increasing temperature. When the temperature stabilized and thermal cracking processes became prevalent, images of the samples darkened following first-order kinetics specific to each feed. The darkening rates of the micrographs showed good correlation with the conversion of 524+° C. material in the case of Athabasca VR. The darkening of the micrographs could have been caused by a gradual increase of the refractive index of the sample, which followed changes in aromaticity. During the decrease of the brightness Intensity, samples underwent a red-to-blue color change. One of two types of reaction behavior was observed, depending on the feed: either a homogeneous color change of the reacting feed (Type-I) or a heterogeneous color change (Type-II) following the formation of an isotropic fouling phase. Regardless of the reaction behavior, the color shift followed a change in spectral absorption which corresponded to the formation of more conjugated molecular species. These changes in molecular conjugation also affected intermolecular dispersion forces, which have a direct impact on solubility behavior. More specifically, the occurrence of the red-to-blue color shift was correlated to the formation of $CS_2$-insoluble material. Eventually, trends in brightness Intensity were reversed with the formation of bright mesophase domains. Mesophase domains appeared shortly after the formation of the isotropic fouling phase in Type-II behaviors, while Type-I behaviors showed large variability in the time gaps between the color shift onset and the mesophase onset. Contrary to assumptions in the prior art, the formation of mesophase was shown to be a very poor indicator of the formation of toluene-insoluble coke.

The evolution of a wide variety of reacting feeds under thermal cracking conditions was examined by a series of micrographs taken as the feeds underwent reaction using a 420° C. setpoint temperature. The behavior of these petroleum samples when subjected to pyrolysis exhibited many similarities. In the first 10 minutes of reaction, an increase in brightness could be observed in all experiments as the reacting medium was heated from 360° C. to 420° C. As the temperature approached its setpoint, this brightness trend reversed and following micrographs began to darken. The apparent darkening of the reacting medium was the dominant observation in all cases through the longest part of the experiments. At some point during the darkening of the sample, the reacting medium underwent a color change and became noticeably bluer. Eventually, the darkening rate of the sample slowed and small bright domains of mesophase material began to appear. These mesophase domains grew in size and number with further reaction time, until the termination of the run. Nevertheless, qualitative observation of the micrographs indicated that the darkening rate, the onset time of color change and the onset time of mesophase formation were specific to each feed. Observations at different temperatures yielded very similar evolution of the micrographs prior to the formation of mesophase, only changing the timescale. More specifically, the dynamic evolution of the brightness and the color changes increased with temperature as the setpoint was increased from 410° C. to 450° C. At 410° C., the growth of mesophase was dominated by the gradual formation of numerous small domains. At 435° C., larger mesophase domains were formed and quickly merged with one another. The trend towards the rapid formation of larger and coalescing domains was even more pronounced at 450° C.

Two main different types of reaction behavior were observed during these experiments, depending on the feed being processed. The first type of behavior (Type I) is defined as when a sample follows a regime where the whole bulk phase undergoes homogeneous color and brightness changes before the formation of mesophase. Athabasca VR, Cerro Negro Crude, Cold Lake bitumen, the Pentane-Extracted Asphaltenes, and Safaniya VR followed Type 1 behavior. A second type of behavior (Type-II) is defined as when a phase separation occurs where domains of blue isotropic material fouled the window surface. In this Type-II behavior, mesophase domains formed much later, and appeared from within the regions previously fouled with blue isotropic material. This type of behavior is exhibited by Colombian VR and Gudao VR.

The differences between Type-I and Type-II behaviors can be explained by the solubility limitations of asphaltenic material. Phase instability may occur in a petroleum feed if large polarizable poly-aromatic molecules are present in a medium rich in shorter and more paraffinic compounds. Under thermal cracking conditions, asphaltenic compounds may undergo side-chain cleavage, aromatization and oligomerization, which increase their sizes, aromaticity and polarizability. At the same time, side chain cleavages tend to enrich the reacting medium in paraffinic molecules, unless they are short enough to evaporate from the liquid phase. As a whole, the bulk of the reacting material becomes a poorer solvent for asphaltenic products as reaction proceeds. In Type-I behavior, reaction products are still able to solvate large poly-aromatic clusters. In Type-II behavior, however, a solubility limit is reached, beyond which asphaltenic products separate out as an isotropic phase.

In the prior art, the onset time of mesophase was taken as a reference for evaluating the induction period, i.e., the reaction time before the formation of fouling material. Mesophase is, however, characterized by optical activity and phase anisotropy, not by a solubility class. The detection of coke, defined as toluene-insoluble material, is the usual reference for describing solubility limitations and fouling behavior. The observation of Type-II reaction behavior showed the occurrence of fouling processes long before the formation of mesophase. Additionally, thermal cracking processes in Pentane-Extracted Asphaltenes followed a Type-I behavior and produced mesophase domains after 60 min of reaction, while complementary ex situ analyses revealed the formation of $CS_2$-insoluble material after 20 min of reaction. Therefore, it is believed that there is a poor correspondence between the formation of mesophase material and the production of coke defined by solubility class. More specifically, these reactions showed that isotropic coke (based on solubility) formed significantly earlier than the onset of anisotropic mesophase (based on optical activity).

Evolution of Brightness Intensity.

Figure 4:
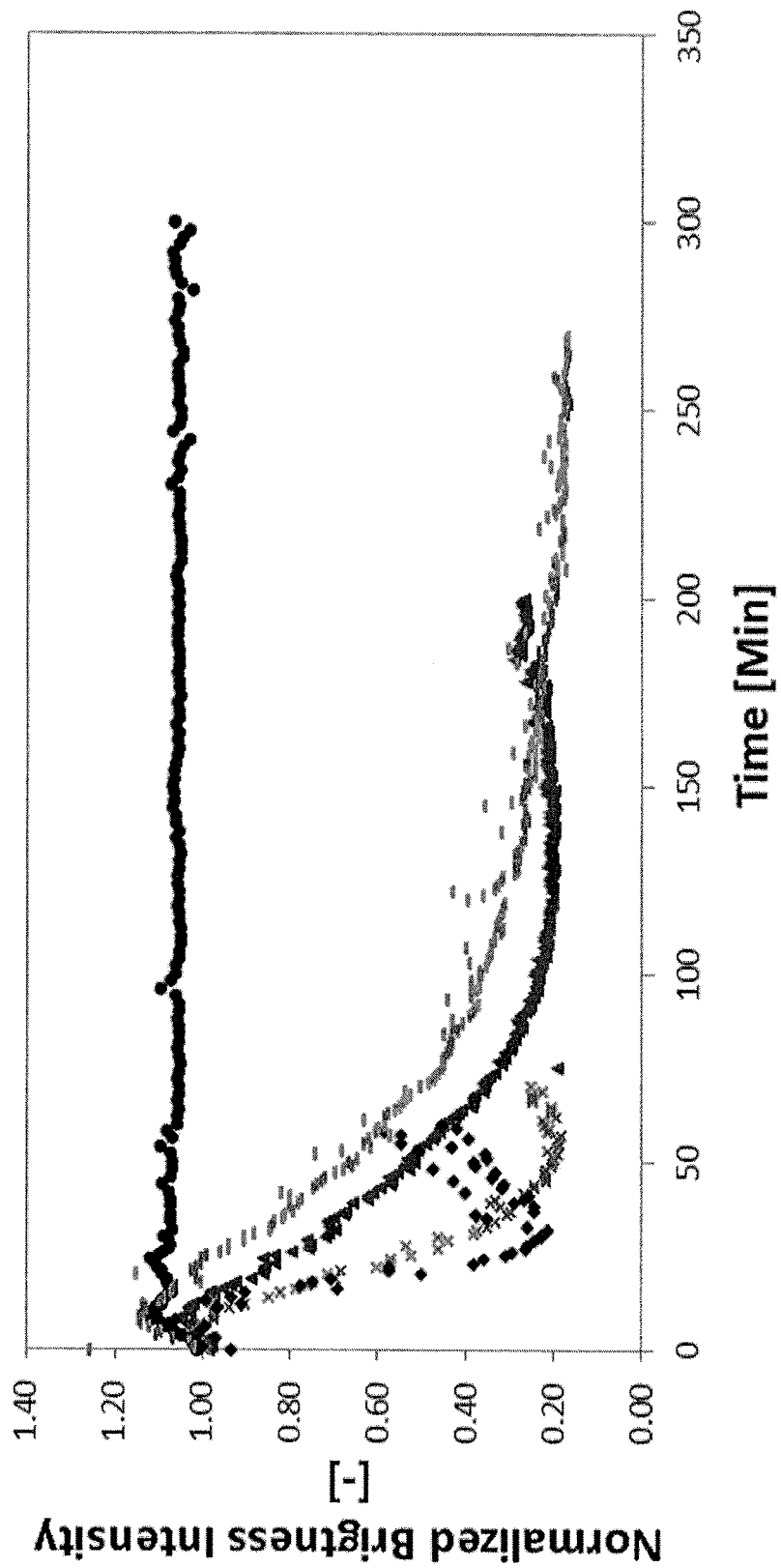
FIG. 4 shows Normalized Brightness Intensity of a feed that follows Type-I reaction behavior. Data from micrographs taken during thermal cracking reactions of Athabasca VR with setpoint temperatures of 330° C. (●), 410° C. (▬) 420° C. (▲), 435° C. (x), 450° C. (♦).
Figure 5:
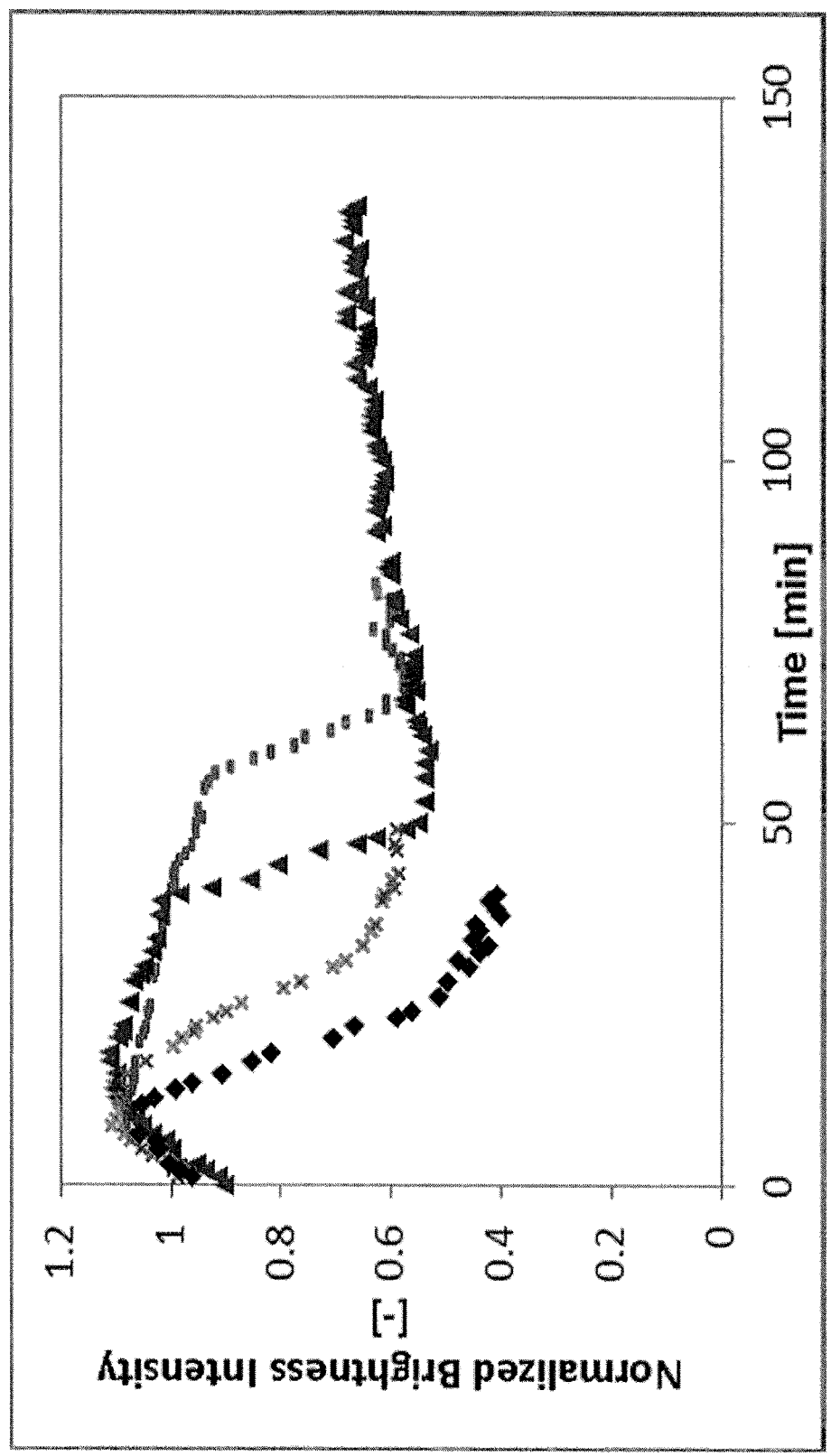
FIG. 5 shows Normalized Brightness Intensity of a feed that follows Type-II reaction behavior. Data from micrographs taken during thermal cracking reactions of Gudao VR with setpoint temperatures of 410° C. (▬), 420° C. (▲), 435° C. (x), 450° C. (♦)

The evolution of the Brightness Intensity characteristic of Type-I and Type-II reaction behavior is illustrated by the results obtained from Athabasca VR, FIG. 4 and Gudao VR, FIG. 5 Error! Reference source not found., respectively. Many illumination artifacts (including the age of the halogen lamp, cleanliness of the optics, heat exposure of the optics, etc.) caused some variability in the intensity of the reflected light between runs. For a consistent comparison, the Intensity of the micrographs taken in each experiment was normalized by the Intensity of the micrograph showing the highest brightness within the same run. A control experiment was conducted on Athabasca VR at 330° C. (line a, FIG. 4), where there was not enough thermal energy to drive thermal cracking in the scale of hours, in order to illustrate that image properties would not evolve at constant temperature in the absence of a chemical process.

Feeds that follow both Type-I and Type-II reaction behaviors exhibit similar trends of Brightness Intensity with reaction time: the Intensity increased in the initial portion of the experiment, then decreased significantly, before a trend reversal in the end of the run. Qualitatively, all the feeds followed the same evolution in Brightness Intensity. However, the rate of change of the Intensity with reaction time was a function of the source of feed and reaction temperature.

Figure 6:
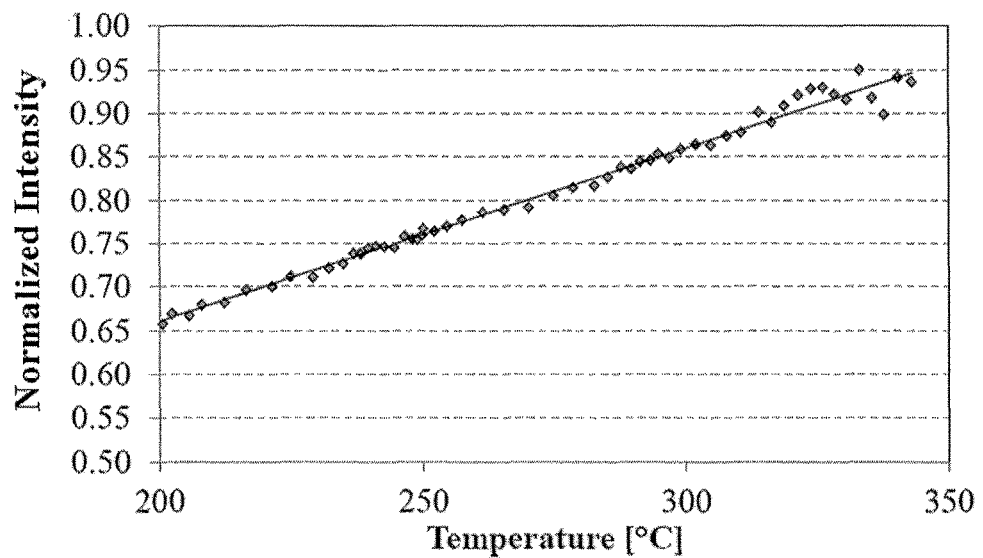
FIG. 6 shows Brightness Intensity as a function of temperature for Athabasca VR at temperatures between 200° and 350° C.

The initial brightness increase seen in all experiments corresponded to the initial portion of the experiment where the reacting material was heated to its temperature setpoint, while the origin of the time axis was set to the instant the sample reached 360° C. The relationship between reflected brightness and sample temperature was further characterized from 200 to 350° C., a temperature range well below thermal cracking conditions for Athabasca VR, as shown on FIG. 6 Error! Reference source not found. Given the slow kinetics of thermal cracking processes occurring in the 360° C.-400° C. temperature range, it can be deduced that the initial Intensity increase at early reaction times is not a chemically-driven process.

Once the temperature was stabilized near its setpoint, thermal cracking processes became prevalent and resulted in the darkening of the sample. The curves shown in FIG. 4 suggest a decreasing exponential behavior following first order reaction kinetics which is characteristic of all feeds following Type-I reaction behavior. Type-II behavior exhibits a precipitous decrease in Brightness part way through the reaction which is caused by the formation of a fouling layer of dark isotropic material.

Figure 7:
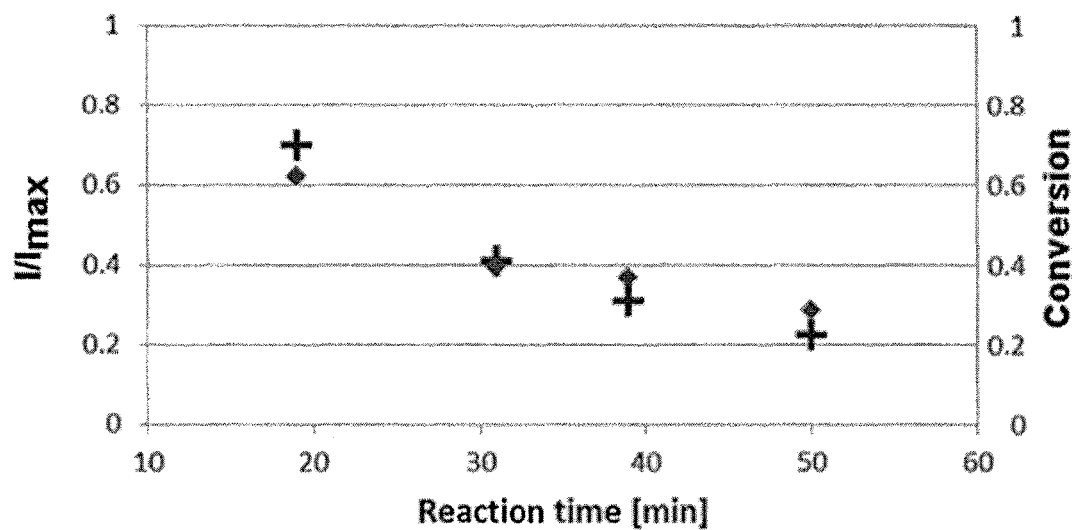
FIG. 7 shows the relationship between Brightness Intensity (♦) and Conversion of 524+° C. (+) in reactions of Athabasca VR at 435° C.

Complementary ex situ analyses were conducted on reaction products from experiments on Athabasca VR at 435° C. to determine the evolution of the content of 524+° C. material in the sample with reaction time. The results, presented in FIG. 7, showed a good agreement between brightness Intensity and conversion of 524+° C. material.

The initial brightening of the sample with increasing temperature and the following darkening of the sample with thermal cracking reactions can be explained by the evolutions of refractive indices. At normal incidence, the intensity of a reflected ray of light (R) at the interface between a C-axis cut sapphire window (refractive index of the extraordinary ray $n_{s,e}$) and an opaque sample (refractive index $n_o$ and extinction coefficient κ) is given by Eq. 11.

$$R = \frac{(n_o - n_{s,e})^2 + \kappa_o^2}{(n_o + n_{s,e})^2 + \kappa_o^2} \quad \text{Eq. 11}$$

At room temperature, the refractive index of sapphire for the extraordinary ray is above 1.75 in the visible light range, while crude oil samples have a refractive index ranging from 1.45 to 1.6, with the refractive index of asphaltenic material estimated around 1.71. There are strong correlations between the density and the refractive index of crude oils. Given that bitumen density decreases at higher temperatures, the refractive index of heavy petroleum samples can be considered as a decreasing function of temperature. The refractive index of sapphire, however, is an increasing function of temperature. Assuming a constant contribution from the light absorption by the oil sample, a temperature increase induces a greater difference between the refractive index of sapphire and that of the oil sample, which enhances the Intensity of the reflected light. When a petroleum sample undergoes thermal cracking reactions at constant temperature, however, the aromaticity of the liquid tends to increase, along with density and refractive index. As a result, the gap between the refractive index of sapphire and that of the oil is reduced, causing a decrease in the Intensity of the reflected light with reaction time.

The change in brightness resulting from the detection of mesophase, however, was not due to changes in refractive index. Instead, the optical activity of this anisotropic material caused significant rotation of the polarization plane of the light upon reflection, which allowed more light to pass through the cross-polarizer module and make these domains look brighter on the micrographs.

Color Changes.

Figure 8:
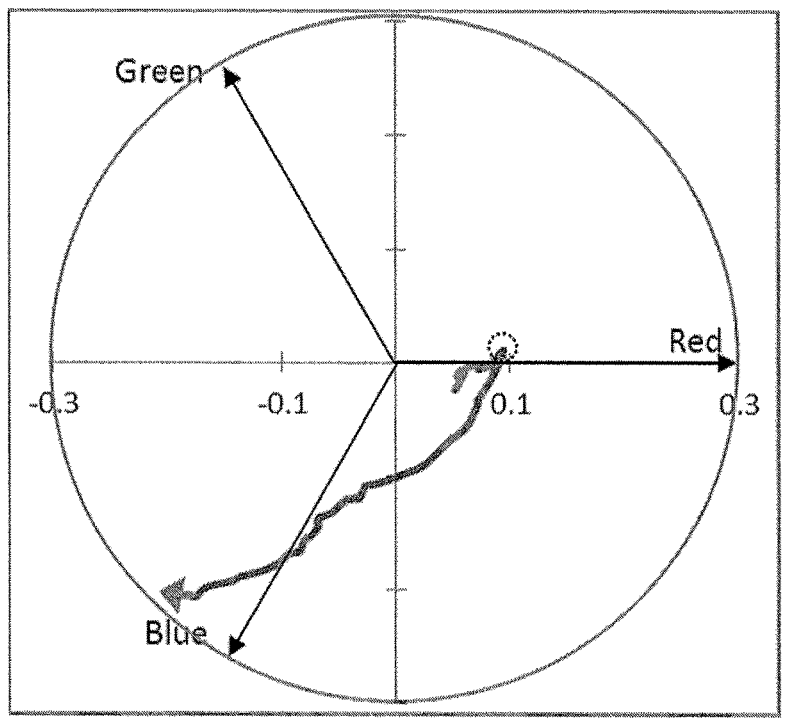
FIG. 8 shows a color-wheel plot indicating red-to-blue shifts in Athabasca VR.
Figure 9:
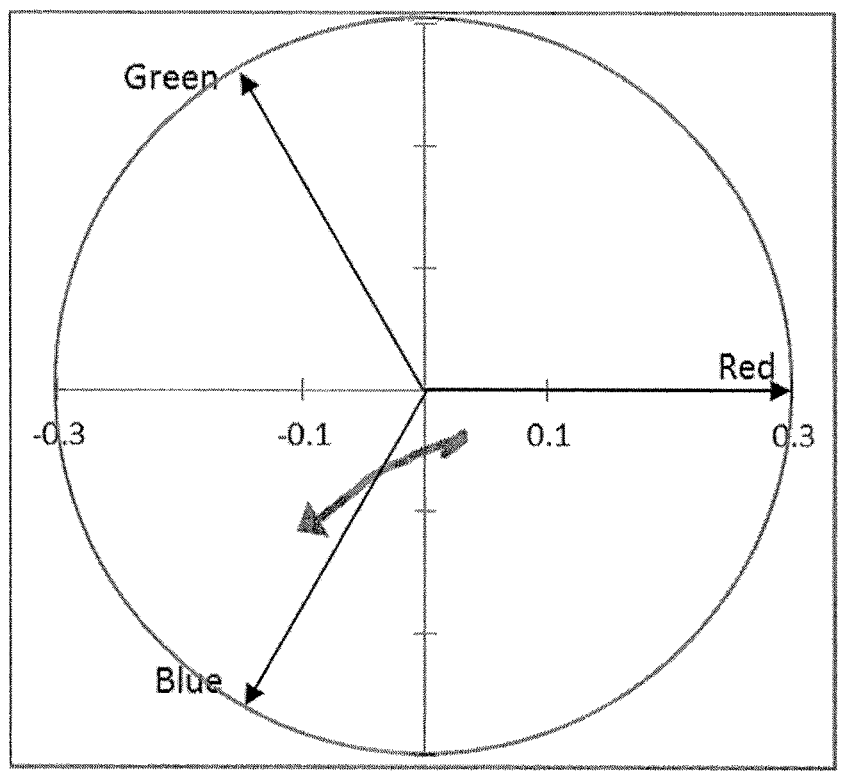
FIG. 9 shows color-wheel plots indicating red-to-blue shifts in Gudao VR.

The color changes in reacting samples are illustrated by the evolution of Hue and Saturation values on colorwheel plots for Athabasca VR and Gudao VR, respectively in FIG. 8 and FIG. 9. All petroleum samples showed a consistent evolution of color under thermal cracking conditions, regardless of reaction temperature, starting from a desaturated reddish color, samples turned blue, and eventually exhibited more saturated blue color. However, color changes in reacting samples were not a linear function of reaction time.

Figure 10:
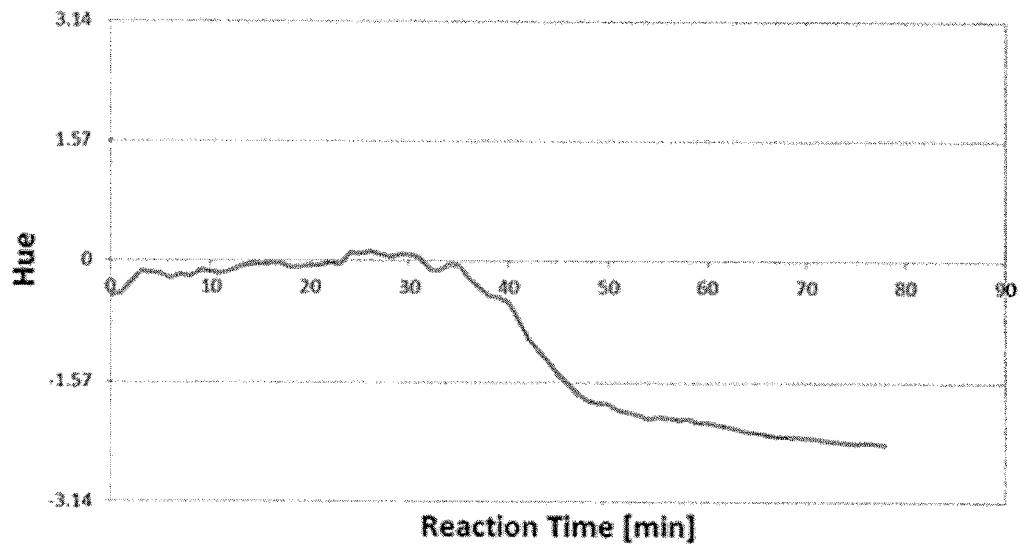
FIG. 10 shows mean Hue of the micrographs during the reaction of Athabasca VR using 435° C. as setpoint temperature.
Figure 11:
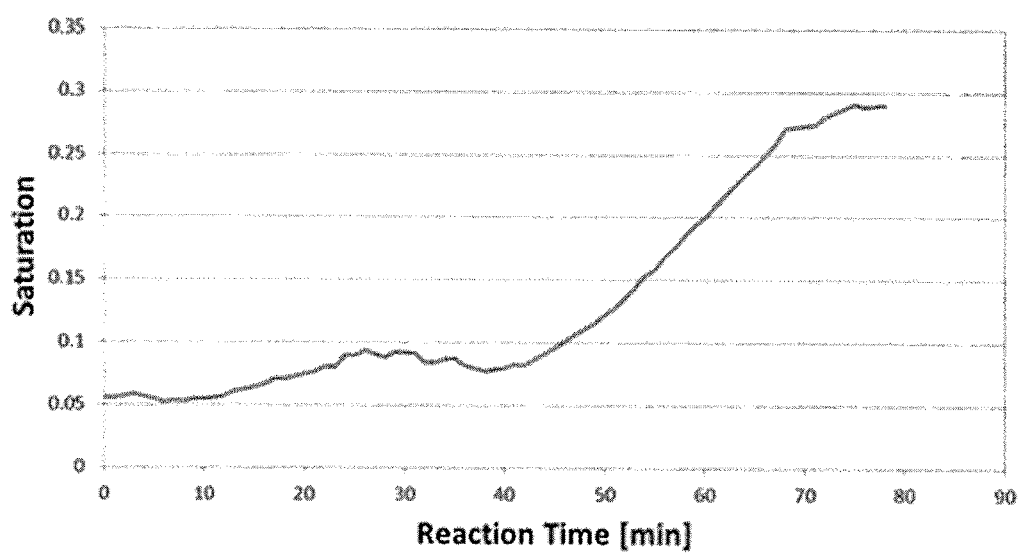
FIG. 11 shows mean Saturation of the micrographs during the reaction of Athabasca VR using 435° C. as setpoint temperature.

For a better description of the typical evolution of sample color with reaction time, the Hue and Saturation plots from the reaction of Athabasca VR at 435° C. (FIG. 8) were decomposed into two functions of time on FIG. 10 (Hue vs. Time) and FIG. 11 (Saturation vs. Time). FIGS. 10 and 11 illustrate that color changes were negligible in the first 10 minutes of the run, while the temperature of the reaction medium increased along with the brightness of the micrographs. Once thermal cracking processes became prevalent and the micrographs began to darken, color changes remained minimal at first, with very slight increases in Hue and Saturation values. In the case of the reaction of Athabasca VR at 435° C., image properties remained stable until approximately 24 mins. The color of the samples then began to change, with subtle decreases in Hue and Saturation values at first, while the darkening rate of the micrographs seemed unaffected. A local maximum in Hue and Saturation values could be observed in thermal cracking reaction for all feeds at all of the setpoint temperatures, which marked the onset of a red-to-blue color shift.

Low saturation levels, digital imaging noise and illumination artifacts may make the identification of the color shift onset difficult. The color transition became gradually more evident afterwards, with a more pronounced decrease in Hue values and a reversal of the Saturation trend (after 40 min in the reaction of Athabasca VR at 435° C.). The later formation of mesophase domains (onset at 60 min in the reaction of Athabasca VR at 435° C.) had little impact on Hue and Saturation trends, while its contribution to the brightness intensity was significant. When the evolution of the reacting medium was dominated by mesophase growth, Hue and Saturation values stabilized.

Figure 12:
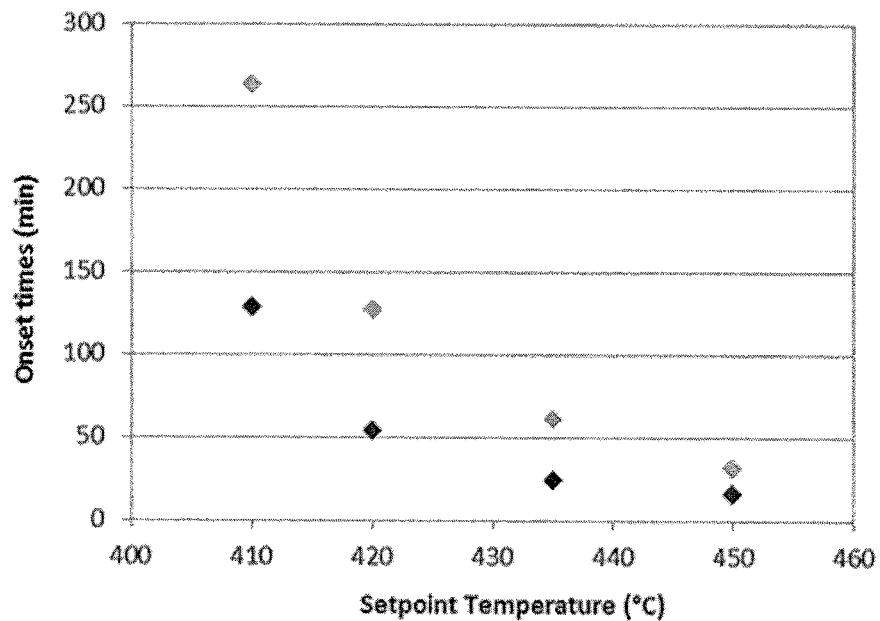
FIG. 12 shows Color shift onset times (dark) and mesophase onset times (light) in reactions of Athabasca VR at 410° C., 420° C., 435° C., and 450° C.

The color shift onset times in reactions of Athabasca VR were reported as a function of the reaction temperature on FIG. 12, where they were compared with the corresponding onset times of mesophase formation. Both the color shift onset time and the mesophase onset time followed decreasing exponential functions of temperature, which can be related to the apparent first-order kinetics of the brightness changes.

Figure 13:
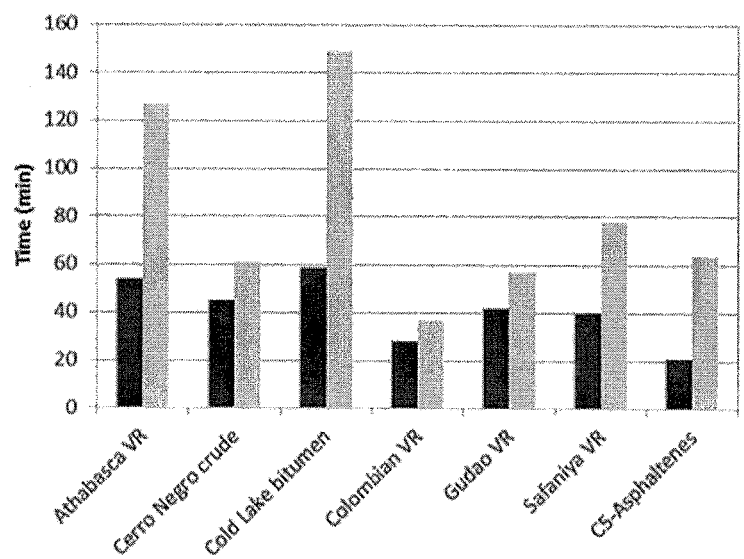
FIG. 13 shows onset times of the red-to-blue color shift (dark grey bars) and mesophase formation (light grey bars) during the thermal cracking of petroleum samples at 420° C.

The Hue and Saturation trends in all runs were the same as those of the reaction of Athabasca VR at 435° C., only with different onset times for the red-to-blue color shift and for the steep increase of the Saturation curve. In samples that exhibited Type-II behavior, the onset of the red-to-blue color shift was induced by the formation of the isotropic fouling layer, whereas the color change seemed homogeneous in samples exhibiting Type-I behavior. Since the expression of mean Hue and Saturation data does not describe textures or patterns in an image, Type-II mean color trends remained similar to Type-I mean color trends. The feed-dependence of the color shift onset time is illustrated in FIG. 13 for experiments at 420° C., and compared with the corresponding onset time of mesophase formation. The shorter color shift onset time was observed in Pentane-Extracted Asphaltenes, which corresponds to the higher propensity of this material to form coke (defined by solubility class). The longer color shift onset time was observed in the case of Cold Lake Bitumen, which also exhibited the longest onset time for mesophase formation. Different feeds showed large variability in the time gaps between the color shift and the formation of mesophase, especially in feeds following a Type-I behavior. Feeds following a Type-II behavior, however, exhibited consistently shorter time gaps between these two phenomena: the destabilization of an isotropic fouling phase out of the bulk promoted its transformation into an anisotropic phase.

The reflected color of a petroleum sample strongly depends on its chemistry. The amount of light that is absorbed by a sample in the visible range is a function of the energy of electronic transitions (i.e., HUMO/LUMO gap) of the molecular species. More conjugated organic molecules require less photonic energy for the electrons to reach an excited state, thus they absorb light at longer (less energetic) wavelength. As a petroleum sample is subject to thermal cracking conditions, the liquid phase undergoes an increase in aromaticity and unsaturated products, yielding more conjugated compounds. Therefore, the absorption spectrum of a reacting oil sample under pyrolysis conditions should shift towards longer wavelengths with increasing reaction time. The reflected color of the oil sample, as observed in microscopy experiments, is the complementary color with respect to the wavelength of spectral absorption. In other words, if a substance predominantly absorbs a certain light color, it will reflect the diametrically opposed color from the colorwheel. The red-to-blue color shifts in petroleum samples under thermal cracking conditions would correspond to a spectral shift in absorption from cyan-blue to yellow, matching the decrease of the HUMO/LUMO gap associated to the formation of more conjugated species.

Figure 14:
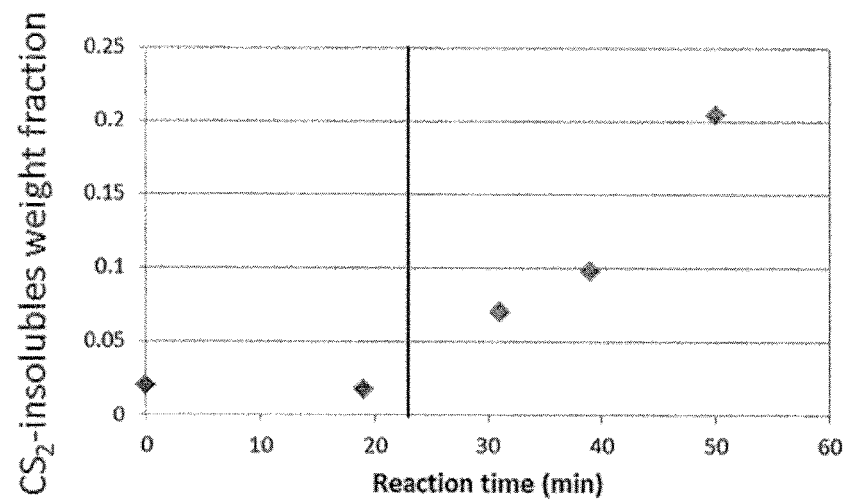
FIG. 14 shows yields of $CS_2$-insoluble material in the liquid products from thermal reactions of Athabasca VR at 435° C. The vertical black line corresponds to the onset of the red-to-blue color shift.

Further ex situ analyses were conducted in order to link the onset of the red-to-blue color shift with solubility properties. Considering color as a descriptor of mean molecular conjugation, a red-to-blue shift should describe an increase in mean molecular polarizability, while the solubility behavior in reacting oils is dominated by the intensity of dispersion forces. Reacted samples from Athabasca VR following experiments at 435° C. were blended with carbon disulfide ($CS_2$) and filtered to determine the amount of insoluble material. Results are reported in FIG. 14 where they are compared with the amount of $CS_2$-insoluble material in the unreacted feed. The data show that the onset of the red-to-blue color shift observed by microscopy (at 24 min of reaction in this case) approximately corresponds to the onset of $CS_2$-insoluble coke. These experiments confirm the formation of isotropic coke under thermal cracking conditions long before the formation of anisotropic mesophase, Since the formation of toluene-insoluble material should occur before the formation of $CS_2$-insoluble material, the onset of toluene-insoluble coke should precede the red-to-blue color shift as well. Notably, none of the feeds exhibited phase separation in situ before the color shift onset, including the cases of Type-II behavior.

Heterogeneity

Figure 15:
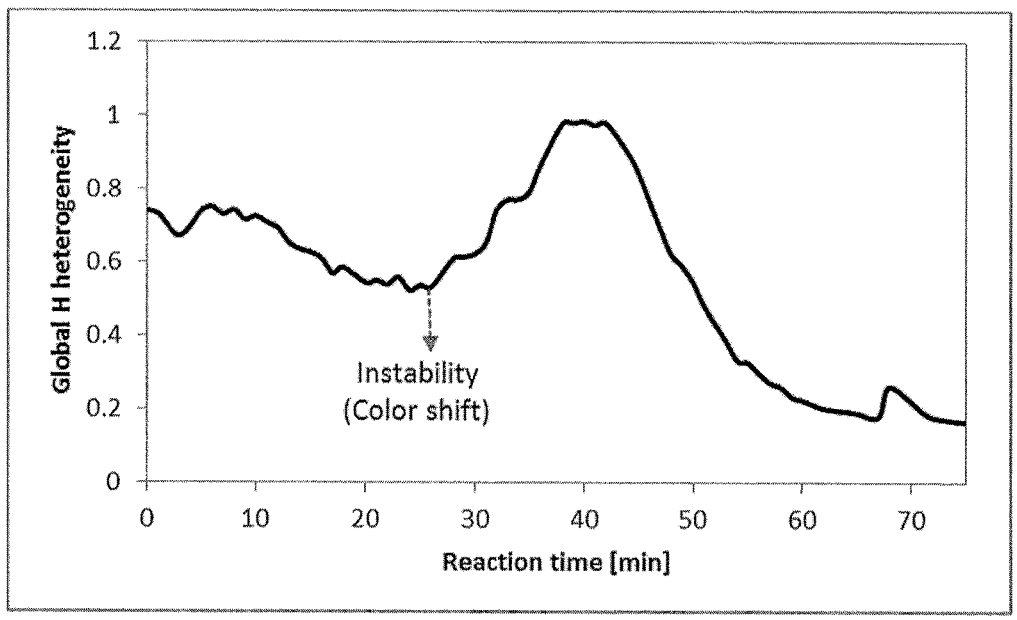
FIG. 15 shows a plot of Global H heterogeneity vs. time for the reaction of Athabasca VR at 435° C., where a significant inflection in the heterogeneity trend (arrow) is seen at about the 26 minute mark.

Global H heterogeneity was calculated as the standard deviation of the H values of all pixels in the image, and plotted against reaction time, shown in FIG. 15. As may be seen, a significant inflection in heterogeneity trend was seen at about 26 minutes where the Global H heterogeneity switched from a decreasing trend to an increasing trend in standard deviation occurred between successive images.

Heavy Petroleum Feeds.

The chemical and physical behavior of a variety of heavy petroleum feeds from around the world was investigated at thermal cracking conditions. The reference feed in this study was the same Vacuum Residue from Athabasca (Canada), Three other Vacuum Residua were used in this investigation: Colombian Heavy, Gudao (China), and Safaniya (Saudi Arabia), Additionally, two bituminous crudes were tested: Cerro Negro (Venezuela) and Cold Lake (Canada), Lastly, complementary experiments were made on pentane-extracted industrial asphaltenes from a Canadian feedstock.

Elemental composition of these feeds was determined using a Thermo Scientific Flash 2000 CHNS-O analyzer. Samples (5-10 mg in weight) were placed in tin capsules and inserted in the apparatus oven at 1500° C. to measure elemental composition. Prior to the measurement of the samples, the characterization method was calibrated using a BBOT (2,5 Bis(5-tert-butyl-2-benzo-oxazol-2-yl) thiophene) standard. Both standard and samples were analyzed in triplicate. Corresponding data are reported in Table 1.

TABLE 1

Elemental composition of the feeds used in thermal cracking experiments.

| Feed | C (wt. %) | H (wt. %) | N (wt. %) | S (wt. %) |
|---|---|---|---|---|
| Athabasca VR | 83.93 ± 0.15 | 9.85 ± 0.11 | 0.76 ± 0.01 | 5.46 ± 0.17 |
| Cerro Negro Crude | 84.99 ± 0.17 | 10.62 ± 0.09 | 0.71 ± 0.03 | 3.68 ± 0.11 |
| Cold Lake bitumen | 84.10 ± 0.15 | 10.39 ± 0.07 | 0.57 ± 0.01 | 4.94 ± 0.10 |
| Colombian VR | 87.84 ± 0.07 | 9.76 ± 0.04 | 0.73 ± 0.03 | 1.67 ± 0.10 |
| Gudao VR | 85.27 ± 0.06 | 11.36 ± 0.05 | 0.90 ± 0.01 | 2.46 ± 0.11 |
| Pentane-Extracted Asphaltenes | 87.20 ± 0.13 | 8.56 ± 0.02 | 1.06 ± 0.01 | 3.18 ± 0.10 |
| Safaniya VR | 84.39 ± 0.13 | 10.07 ± 0.01 | 0.54 ± 0.01 | 5.00 ± 0.13 |

Hot-stage Reactor.

Experiments were carried out with a hot-stage reactor which was made from an assembly of Swagelok and Parker stainless steel fittings fitted with a sapphire window at the bottom to allow for observations using an inverted microscope, as shown in Error! Reference source not found., The sapphire window, provided by Guild Optical Associates, was 20 mm in diameter, 3 mm thick, and cut with the C-axis normal to the faces in order to minimize birefringence. The seal between the sapphire window and the stainless steel fitting was made by the compression of a silver-plated stainless steel O-ring from Unified Alloys. Temperature of the reacting media inside the reactor was measured using a Omegaclad XL type K 1/16" thermocouple that was located less than 1 mm away from the sapphire surface. The liquid sample inside the reactor was stirred by means of a custom-machined Alnico magnet (9×4×3 mm) with a center hole. The thermocouple was used as a shaft to center the location of the magnet within the reactor. This Alnico magnet was driven by the rotation of a larger (1" diameter×6" long) Alnico magnet at 120 rpm, away from the reactor. A 1/16" Swagelok front ferrule was inserted at the tip of the thermocouple to maintain a clearance gap between the rotating magnet and the surface of the sapphire window.

The reactor was inserted into a stainless steel block heated by a 300 W coiled stainless steel sheath heater provided by O.E.M. Heaters. The heater and the reactor were kept inside a stainless steel casing filled with ceramic wool for insulation purposes. Temperature regulation was managed by means of a Omron ESCN PID controller.

Cross-Polarized Microscopy.

Observations of the reacting materials were performed using a Zeiss Axio Observer.D1m inverted microscope. Samples were illuminated by a 100 W halogen lamp and observed through a cross-polarizer reflector module using 100× magnification. The polarization plane of the light was slightly changed when traveling through sapphire despite the C-axis cut, which allowed for the observation of isotropic material using cross-polarizers. In contrast, observation of isotropic samples through a non-birefringent YAG window only yielded black micrographs. Images were recorded using a Zeiss AxioCam ICC3 camera which was connected to a desktop computer. The field of view described by the images was approximately 1.19×0.88 mm.

Experiments were carried out in semi-batch conditions at atmospheric pressure, where the liquid remained at the bottom of the reactor while a vent line was open to allow the release of gas products. In each experiment, the sample was initially set under atmospheric nitrogen pressure and heated to 350° C. as a baseline temperature, before switching to a chosen temperature setpoint for the reaction (either 410° C., 420° C., 435° C., or 450° C.). As the temperature in the reactor passed the threshold of 360° C., which can be approximately considered the onset of thermal cracking in the timescale of refining processes, a first micrograph was taken and referred to "time 0" and subsequent cross-polarized micrographs were taken every minute. When not collecting images, the microscope objective was moved away from the heated zone of the reactor in order to prevent overheating of the optics. Experiments were terminated once mesophase domains covered a significant fraction of the window surface.

Ex Situ Analyses.

Complementary ex situ analyses were carried out following reactions of Athabasca VR at 435° C. in order to assess reaction conversion and solubility behavior of reacted products. Samples underwent thermal cracking before quenching at specific reaction times using cold air generated from an Exair vortex tube, which achieved cooling rates down to −150° C./min. The recovered liquid products were blended with carbon disulfide ($CS_2$) at a 1:200 volume ratio, before being filtered to determine the yield of $CS_2$-insoluble coke. Carbon disulfide appeared a posteriori as the best solvent for linking optical properties of reaction products with their solubility properties. After complete evaporation of carbon disulfide, the remaining products were analyzed by SimDist (following ASTM D7169 method) to determine the amount of 524+° C. material in the reacted products.

The SimDist apparatus was based on a Varian 450-GC Gas Chromatograph operated with an Agilent Capillary Column, CP-SimDist CB High Temp (length: 5 m; inner diameter: 0.53 mm; film thickness: 0.09 μm). The unit was operated with the chromatography software CompassCDS, Version 3.0.0.68 (Bruker). The chromatograms were processed and integrated with the software SimDist Reporter—Bruker Compass, Version 4.0.0. The recovery calculation was made using the response factor of the standard sample, the total area of the sample chromatogram, and the concentration of the sample.

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

REFERENCES

The following references are incorporated herein by reference (where permitted) as if reproduced in their entirety. All references are indicative of the level of skill of those skilled in the art to which this invention pertains.

Gray, M. R. *Upgrading Petroleum Residues and Heavy Oils*; Marcel Dekker Inc.: New York, USA, 1994.

Wiehe, I. A. *Process Chemistry of Petroleum Macromolecules*; CRC Press: Boca Raton, USA, 2008.

Wiehe, I. A.; Kennedy, R. J. Application of the Oil Compatibility Model to Refinery Streams, Energy Fuels, 2000, 14, 60-63.

Wiehe, I. A. A Phase-Separation Kinetic Model for Coke Formation. *Ind. Eng. Chem. Res.*, 1993, 32, 2447-2454.

N. E. Burke, R. E. Hobbs, S. F. Kashou. Measurement and Modeling of Asphaltene Precipitation. *J. Pet. Technol.*, 1990, 42, 1440-1446.

Bagheri, S. R.; Gray, M. R.; McCaffrey, W. C. Influence of Depressurization and Cooling on the Formation and Development of Mesophase. *Energy Fuels*, 2011, 25, 5541-5548.

Bagheri, S. R.; Gray, M. R.; Shaw, J.; McCaffrey, W. C. In Situ Observation of Mesophase Formation and Coalescence in Catalytic Hydroconversion of Vacuum Residue Using a Stirred Hot-Stage Reactor. *Energy Fuels*, 2012, 26, 3167-3178.

Bagheri, S. R.; Gray, M. R.; McCaffrey, W. C. Depolarized Light Scattering for Study of Heavy Oil and Mesophase Formation Mechanisms. *Energy Fuels*, 2012, 26, 5408-5420.

Brooks, J. D.; Taylor, G. H. Formation of Graphitizing Carbons from the Liquid Phase, *Nature*, 1965, 32, 697-699.

Chwastiak, S.; Lewis, R. T.; Ruggiero, J. D. Quantitative Determination of Mesophase Content in Pitch. *Carbon*, 1981, 19, 357-363.

R. T. Lewis, Hot-Stage Microscopy of Mesophase Pitches. Ext. Abstr. 12th Bienn. Am. Conf, Carbon, Am. Carbon Soc. 1975, 215-216.

Perrotta, A. J.; McCullough, J. P.; Beuther, H. Pressure-Temperature Microscopy of Petroleum-Derived Hydrocarbons, Prepr. Pap. *Am. Chem. Soc., Div. Pet. Chem.*, 1983, 28, 633-639.

Rodriguez, J.; Tierney, J. W.; Wender, I. In Situ Evaluation of the Carbonization Behavior of Graphitizable Carbon Precursors. *Am. Chem. Soc. Div. Fuel Chem.*, 1991, 36, 1081-1087.

Lafdi, K.; Bonnamy, S.; Oberlin, A. Mechanism of Anisotropy Occurrence in a Pitch Precursor of Carbon-Fibers: 3, Hot Stage Microscopy of Pitch-B and Pitch-C. *Carbon*, 1991, 29, 857-864.

Rahimi, P.; Gentzis, T.; Dawson, W. H.; Fairbridge, C.; Khulbe, C.; Chung, K.; Nowlan, V.; DelBianco, A. Investigation of Coking Propensity of Narrow Cut Fractions from Athabasca Bitumen Using Hot-Stage Microscopy, *Energy Fuels*, 1998, 12, 1020-1030.

ASTM D156-15. Standard Test Method for Saybolt Color of Petroleum Products (Saybolt Chromometer Method). ASTM International: Conshohocken, USA, 2015.

Andrews, R. J.; Beck, G.; Castelijns, K.; Chen, A.; Cribbs, M. E.; Fadnes, F. H.; Irvine-Fortescue, J.; Williams, S.; Hashem, M.; Jamaluddin, A.; Kurkjian, A.; Sass, B.; Mullins, O. C.; Rylander, E.; Van Dusen, A. Quantifying Contamination Using Color of Crude and Condensate. *Oilfield Review*, 2001, Autumn 2001, 24-43.

Mullins, O. C.; Sheu, E. Y. *Structures and Dynamics of Asphaltenes*. Plenum Press: New York, USA, 1998.

Mullins, O. C.; Sheu, E. Y.; Iammami, A.; Marshall, A. G. *Aspahltenes, Heavy Oils and Petroleomics*. Springer: New York, USA, 2007.

Speight, J. G. The Chemistry and Technology of Petroleum, Fifth Edition, CRC Press: Boca Raton, USA, 2014.

What is claimed is:

1. A method of determining the propensity of a petroleum feed to form fouling material, comprising the steps of:
   a) subjecting a sample of the petroleum feed to reaction conditions to induce one or more chemical and/or physical changes, while illuminating the sample with cross-polarized light;
   b) collecting light reflected by the sample over a period of time to produce a plurality of digital images, each comprising a plurality of pixels; and
   c) analyzing spectral properties of the collected light and determining a measure of heterogeneity of the sample, where an increase in heterogeneity is indicative of initiation of fouling formation; and
   d) wherein the digital images are analyzed to yield values for hue (H), saturation (S), or intensity (I) for each pixel of the image or a selected portion of the pixels of the image, wherein the analysis comprises the step of computing a standard deviation of H and/or S and/or I values for each pixel in a selected local region of pixels, and summing the values obtained for each local region to yield local heterogeneity descriptors.

2. The method of claim 1 wherein the light is collected by a light collector comprising a hyperspectral sensor, a CMOS or CCD camera, or an imaging spectrophotometer.

3. The method of claim 2, wherein the light collector is configured to transfer the spectral properties to a computer, which is configured to analyze the spectral properties in step (c).

4. The method of claim 1, further comprising computing a standard deviation of H and/or S and/or I values of each pixel of the image to yield a global heterogeneity descriptors.

5. The method of claim 4 wherein an increase in heterogeneity is marked by a 10%, 15% or 20% increase in a standard deviation of a global heterogeneity descriptor, or a minimum exhibited by a shift from a decreasing trend to an increasing trend in a global heterogeneity descriptor.

6. The method of claim 4 wherein an increase in heterogeneity is manifest as a red-to-blue color shift, determined by an apex point marking a change of direction on a plot of data on a color wheel.

7. The method of claim 4 wherein an increase in heterogeneity is manifest as a red-to-blue color shift, determined by a local maximum in a Hue or Saturation value over time.

8. The method of claim 1 wherein an increase in heterogeneity is marked by a 10%, 15% or 20% increase in a standard deviation of a global or local heterogeneity descriptor, or a minimum exhibited by a shift from a decreasing trend to an increasing trend in global or a local heterogeneity descriptor.

9. The method of claim 1 wherein a red-to-blue color shift is determined by an apex point marking a change of direction on a plot of data on a color wheel.

10. The method of claim 1 wherein a red-to-blue color shift is determined by a local maximum in a Hue or Saturation value over time.

11. The method of claim 1 which is implemented with a reactor comprising a sealed reactor body, a window and a cross-polarized microscope.

12. The method of claim 11 wherein the window comprises an optically transparent, birefringent material.

13. The method of claim 12 wherein the window comprises sapphire.

14. The method of claim 13 wherein the microscope is inverted below the window.

* * * * *